United States Patent [19]
Kohno et al.

[11] Patent Number: 5,647,359
[45] Date of Patent: Jul. 15, 1997

[54] MEASURING APPARATUS

[75] Inventors: Hiromasa Kohno; Masaru Kurio, both of Nakai-machi, Japan

[73] Assignee: Terumo Kabushiki Kaisha, Tokyo, Japan

[21] Appl. No.: 221,234

[22] Filed: Mar. 31, 1994

[30] Foreign Application Priority Data

Apr. 1, 1993 [JP] Japan .................................. 5-075542
May 17, 1993 [JP] Japan .................................. 5-114657

[51] Int. Cl.$^6$ .................................................. A61B 5/00
[52] U.S. Cl. .................................................. 128/634; 128/692
[58] Field of Search ..................... 128/633–4, 664–7, 128/692; 356/39–41

[56] References Cited

U.S. PATENT DOCUMENTS

| | | |
|---|---|---|
| 4,453,218 | 6/1984 | Sperinde et al. . |
| 4,523,279 | 6/1985 | Sperinde et al. . |
| 4,651,741 | 3/1987 | Passafaro . |
| 4,796,636 | 1/1989 | Branstetter et al. . |
| 4,859,057 | 8/1989 | Taylor et al. .......................... 128/633 X |
| 4,883,353 | 11/1989 | Hausman et al. ..................... 128/633 X |
| 5,168,873 | 12/1992 | Seiffert et al. ............................ 128/634 |
| 5,190,038 | 3/1993 | Polson et al. ............................ 128/633 |

FOREIGN PATENT DOCUMENTS

0 467 213  1/1992  European Pat. Off. .

*Primary Examiner*—Angela D. Sykes
*Attorney, Agent, or Firm*—Burns, Doane, Swecker & Mathis, LLP

[57] ABSTRACT

Light components are radiated into a blood vessel from light-emitting diodes (17, 18) for emitting light components having different wavelengths through an optical fiber. Bight components reflected by the blood upon radiation into the blood vessel are received by a photo transistor (19) to detect their reflected light intensities. For example, a minimum value of the reflected light intensity of the light component from the light-emitting diode (18) is obtained from the reflected light intensities detected within a predetermined period of time. A measurement value is calculated using this minimum value and a minimum value of the reflected light intensity of the light component from the corresponding light-emitting diode (17).

17 Claims, 8 Drawing Sheets

| MIN / BL | POINT | MIN / BL | POINT |
|---|---|---|---|
| 0.9 < 1.1 | 0 | 1.1 < 1.2 | 1 |
| 0.8 < 0.9 | 1 | 1.2 < 1.3 | 2 |
| 0.7 < 0.8 | 2 | 1.3 < 1.4 | 3 |
| 0.6 < 0.7 | 3 | 1.4 < 1.5 | 4 |
| 0.5 < 0.6 | 4 | 1.5 < 1.6 | 6 |
| 0.4 < 0.5 | 6 | 1.6 < 1.7 | 8 |
| 0.3 < 0.4 | 9 | 1.7 < | 10 |
| 0.2 < 0.3 | 12 | | |
| 0.2 | 15 | | |

FIG. 8

| NCV | POINT | NCV | POINT |
|---|---|---|---|
| 0 | 0 | -6 | 6 |
| -1, 1, 2, 3, 4 | 1 | -7 | 8 |
| -2, 5, 6, 7 | 2 | -8 | 11 |
| -3, 6, 9, 10 | 3 | -9 | 14 |
| -4 | 4 | -10 | 18 |
| -5 | 5 | | |

FIG. 9

| DATA COUNT N | POINT |
|---|---|
| 10 OR MORE | 0 |
| 7, 8, 9 | 1 |
| 4, 5, 6 | 3 |
| 1, 2, 3 | 5 |
| 0 | 10 |

FIG. 10

| SRP | TOTAL NUMBER OF POINTS |
|---|---|
| 9 | 0 |
| 8 | 1 |
| 7 | 2 |
| 6 | 3, 4 |
| 5 | 5, 6 |
| 4 | 7, 8 |
| 3 | 9, 10 |
| 2 | 11, 12, 13 |
| 1 | 14, 15, 16 |
| 0 | 17 OR MORE |

MEASURING APPARATUS

BACKGROUND OF THE INVENTION

1. Field of the Invention

The present invention relates to a measuring apparatus and, more particularly, to a measuring apparatus for radiating light in blood to measure e.g., the oxygen saturation of the blood in accordance with a reflected light intensity.

2. Description of the Related Art

In recent years, a system or apparatus has been developed in which light is radiated in blood through an optical fiber incorporated in a cardiac catheter, and the intensity of a light component of all the radiated light component, which is reflected by the blood, is measured to monitor the oxygen saturation ($SVO_2$) of a mixed venous blood in accordance with the light-absorbing characteristics of hemoglobin. This oxygen saturation monitor for the mixed venous blood plays an important role in detecting and alarming an abrupt change in operating states of circulatory organs in patient's management upon a direct vision intracardiac operation. In addition, this oxygen saturation monitor is useful in evaluating a certain load on a living body, such as drug administration.

When the oxygen saturation is to be measured using such a system or apparatus, various factors except for the oxygen saturation in blood are considered as factors for varying the intensity of light reflected by blood. It is important to suppress the influences of these factors. Some factors may be based on a measuring system, but variation factors derived from a living system are more important. It is, therefore, essential to correct measurement data varied by these variation factors in development of a monitor system.

A system for measuring and monitoring the oxygen saturation will be exemplified. To continuously monitor the oxygen saturation in human blood, light components having two specific wavelengths are radiated in blood using a catheter or the like, and back-scattered light components (reflected light components) from the blood are detected. The specific wavelengths here are defined as a wavelength (isosbestic wavelength: 805 nm) at which the absorbency of oxyhemoglobin is equal to that of reduced hemoglobin and a wavelength (660 nm) at which a difference between the absorbencies thereof becomes large. An intensity signal of reflected light having a wavelength of 805 nm as the isosbestic wavelength rarely depends on the oxygen saturation. However, an intensity signal of reflected light having the wavelength of 600 nm greatly changes depending on the oxygen saturation. These two signals are compared to obtain the oxygen saturation of blood.

An equation for calculating the oxygen saturation during its continuous monitoring was reported by Polanyi et al. in 1960 as follows:

Oxygen Saturation=$A+B$×(Reflected Light Intensity of Near-Infrared Ray)/(Reflected Light Intensity of Red Light)

where A and B are the constants.

In this equation, a ratio of the reflected light intensity at one wavelength to that at the other wavelength is calculated. For this reason, influences such as a change in blood velocity and sizes of blood cells can be canceled to a considerable degree. However, influences on these reflected light intensities by the hematocrit value are different from each other. For this reason, the influences by the hematocrit value cannot be canceled each other even if their ratio is obtained.

Therefore, the above equation cannot be expected to obtain a sufficiently high precision.

The following equation is used for hematocrit correction:

Oxygen Saturation = $A' + B' \times$ (Reflected Light Intensity of Near-Infrared Ray + Correction Term 1)/Reflected Light Intensity of Red Light + Correction Term 2)

where terms 1 and 2 are values experimentally determined to minimize the influences of the hematocrit value, and A' and B' are constants.

This calculation method is effective in monitoring using a sensor probe fixed to a blood circuit such as extracorporeal circulation. However, an $SVO_2$ monitor probe is generally incorporated in the form which adds a function to a catheter for measuring a cardiac minute volume, like a thermal dilution method (so-called Swan-Ganz method). Therefore, the position of a probe sensor is not fixed in a pulmonary artery. The measured intensity of light reflected by blood may include light reflected by the wall of a blood vessel and a valve in an unknown proportion.

This possibility will be considered in detail. A radiating portion for radiating light for measuring the oxygen saturation in blood, and a portion for receiving light reflected by the blood are generally constituted by optical fibers. A fiber opening for radiating light and a fiber opening for receiving reflected light are formed at the distal end of a probe. When the distal end portion of the probe comes close to the wall of the blood vessel at an angle of almost 90° with respect to the longitudinal direction of the catheter, the opening for receiving reflected light receives light reflected by the blood and light reflected by the inner wall of the blood vessel, thereby increasing the intensity of the reflected light. In many cases, the detected intensity of the reflected light may greatly vary in synchronism with a blood flow and respiration. In addition, when the probe comes close to or is brought into contact with the wall of the blood vessel in a state wherein the distal end portion of the probe is held at an angle of almost 180° with respect to the longitudinal direction of the catheter, most of the light reflected by the wall of the blood vessel is reflected forward. For this reason, the intensity of light reflected by the wall of the blood vessel and incident on the fiber opening for receiving the reflected light is very low. The variations in the reflected light intensity synchronized with the blood flow and respiration may be extremely attenuated.

SUMMARY OF THE INVENTION

The present invention has been made in consideration of the conventional examples, and has as its object to provide a measuring apparatus capable of performing accurate measurement using a catheter or the like in a blood vessel.

It is another object of the present invention to provide a measuring apparatus capable of substantially eliminating influences of light reflected by the wall of a blood vessel and accurately measuring the oxygen saturation of blood.

It is still another object of the present invention to provide a measuring apparatus capable of removing a noise component included in a reflected light intensity and performing highly accurate measurement.

It is still another object of the present invention to provide a measuring apparatus capable of analyzing a signal to numerically express the degree of reliability of a measurement value and notifying an operator of the measurement value and the numerical value of signal analysis, thereby improving the reliability of the measurement value.

It is still another object of the present invention to provide a measuring apparatus capable of easily determining the degree of reliability of measured living body information.

In order to achieve the object, the present invention comprises;

A measuring apparatus comprising:
  radiating means for radiating light components having first and second wavelengths different from each other in blood;
  detecting means for detecting reflected light intensities from the blood upon radiation of the light components having the first and second wavelengths;
  minimum value detecting means for detecting a minimum value of the reflected light intensity of one of the light components having the first and second wavelengths detected by said detecting means within a predetermined period of time; and
  calculating means for calculating an oxygen saturation on the basis of the minimum value detected by said minimum value detecting means and a minimum value of the reflected light intensity of the other light component corresponding to the minimum value detected by said minimum value detecting means.

Other features and advantages of the present invention will be apparent from the following description taken in conjunction with the accompanying drawings, in which like reference characters designate the same or similar parts throughout the figures thereof.

DESCRIPTION OF THE PREFERRED EMBODIMENTS

Preferred embodiments of the present invention will be described with reference to the accompanying drawings.

Figure 1:
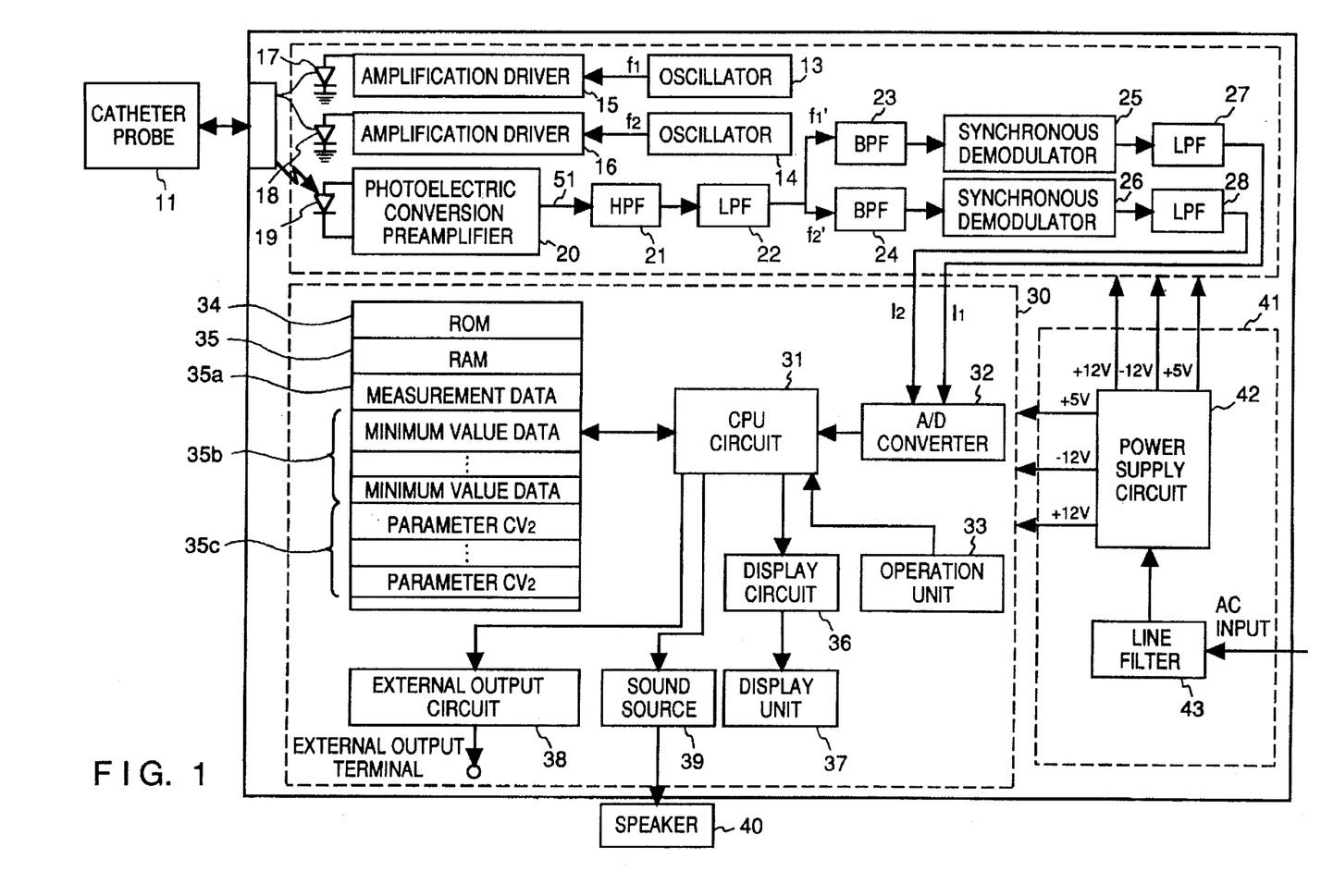
FIG. 1 is a block diagram showing the schematic arrangement of an oxygen saturation measuring apparatus according to an embodiment of the present invention.

FIG. 1 is a block diagram showing the schematic arrangement of an oxygen saturation measuring apparatus according to the first embodiment of the present invention.

Referring to FIG. 1, reference numerals 13 and 14 denote oscillators for outputting AC (sine waveform) signals having different frequencies (f1 and f2). Reference numerals 15 and 16 denote amplification drivers for amplifying the AC signals input from the oscillators 13 and 14 and driving and causing light-emitting diodes 17 and 18 to emit light beams, respectively. Therefore, the light-emitting diode 17 emits light which has a wavelength of 600 nm and flickers at the frequency f1. The light-emitting diode 18 emits light which has a wavelength of, e.g., 805 nm and flickers at the frequency f2.

The optical signals emitted from these two light-emitting diodes 17 and 18 are radiated in blood (not shown) from a catheter probe 11 through optical fibers such as polymethyl methacrylate (PMMA) silica glass. Light reflected by the blood is sent to and detected by a photodiode 19 through the optical fibers. Reference numeral 20 denotes a photoelectric conversion preamplifier 20. The photoelectric conversion preamplifier 20 converts a current output from the photodiode 19 into a voltage signal 51. This voltage signal 51 is a voltage signal obtained by multiplexing the intensity signal of the reflected light which flickers at the frequency f1 and the intensity signal of the reflected light which flickers at the frequency f2. Reference numeral 21 denotes a high-pass filter (HPF); and 22, a low-pass filter (LPF). The noise component included in the voltage signal 51 can be cut off by these filters 21 and 22.

Reference numerals 23 and 24 denote bandpass filters (BPFs). The bandpass filter 23 filters a signal in a frequency band f1' having the frequency f1 as substantially the center frequency. The bandpass filter 24 filters a signal in a frequency band f2' having the frequency f2 as substantially the center frequency. Signals separated by the bandpass filters 23 and 24 are an electrical signal modulated with the frequency f1 and an electrical signal modulated with the frequency f2. Reference numerals 25 and 26 denote synchronous demodulators. The synchronous modulator 25 synchronously detects the signal component having the frequency f1, and the synchronous demodulator 26 synchronously detects the signal component having the frequency f2.

For example, the reflected light intensity signal of light emitted from the light-emitting diode 17 can be extracted by the synchronous demodulator 25, and the signal component having the frequency f1 can be removed from the extracted signal component by a low-pass filter (LPF) 27. The intensity signal of light reflected by the blood upon radiation from the light-emitting diode 17 can be output. Similarly, the reflected light intensity signal of light emitted from the light-emitting diode 18 is extracted by the synchronous demodulator 26, and the intensity signal of light reflected by the blood upon radiation from the light-emitting diode 18 can be output.

A controller 30 causes an A/D converter 32 to convert reflected light intensity signals I1 and I2 of light from the corresponding light-emitting diodes into digital signals. The digital signals are input to a CPU circuit 31. The CPU circuit 31 includes, e.g., a microprocessor. The CPU circuit 31 performs arithmetic and control operations in accordance with control programs stored in a ROM 34 and various data. A RAM 35 is used as a work area for the CPU 31. The RAM 35 serves as a memory for temporarily storing various data. Reference numeral 33 denotes an operation unit operated by an operator to start the measurement and input various functional commands. A display unit 37 is driven by a display circuit 36 to display a message and measurement results to the operator. Reference numeral 38 denotes an external output circuit for outputting measurement data and the like to an external device such as a computer or printer connected through an external output terminal. Reference numeral 40 denotes a speaker for producing an alarm sound using a sound source 39.

Reference numeral 41 denotes a power supply circuit for receiving AC 100 V and generating various power supply voltages used in the apparatus. Reference numeral 42 denotes a power supply circuit such as a switching regulator for outputting various DC voltages, as shown in FIG. 1. Reference numeral 43 denotes a line filter arranged in a power supply line to attenuate power supply noise input through an AC line. Note that the CPU circuit 31 calculates the oxygen saturation on the basis of digital values representing reflected light intensity ratios for the respective wavelengths, the digital values being output from the A/D converter 32.

The data structure of the RAM 35 will be described below. Reference numeral 35a denotes a measurement data area for storing data corresponding to the reflected light intensity signals I1 and I2 measured every 20 ms, as described above. The measurement data area has a capacity for storing at least 50 data. Reference numeral 35b denotes a minimum value data area for sequentially storing minimum value data for each second. Reference numeral 35c denotes a parameter CV2 area for storing a parameter CV2 calculated by an equation (to be described later). In addition to these areas, areas for storing a smallest value MIN, a largest value MAX, a reference intensity BL, and the like are provided.

Figure 2A:
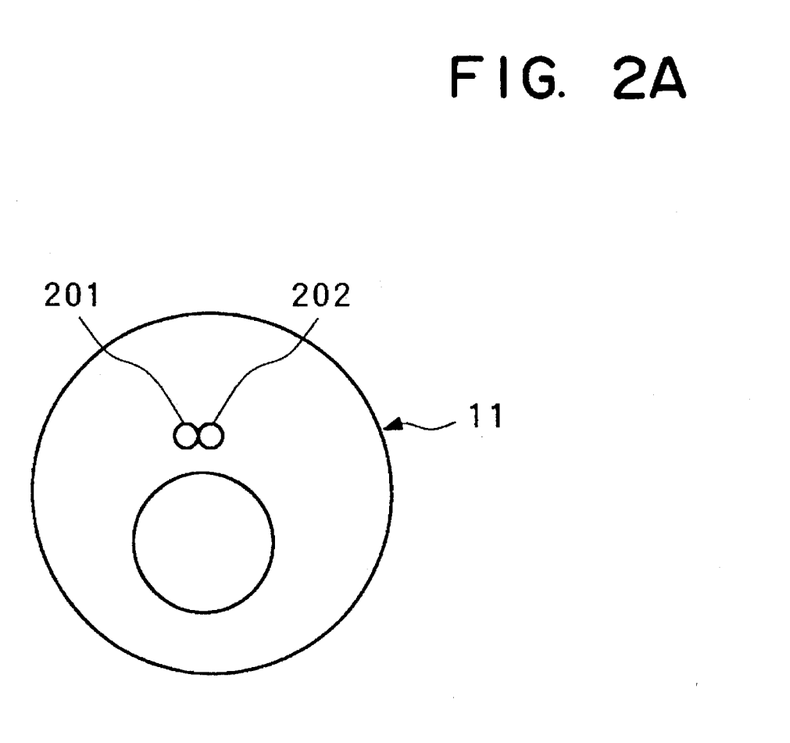
FIGS. 2A and 2B are views showing the shape of a catheter probe connected to the oxygen saturation measuring apparatus according to this embodiment.
Figure 2B:
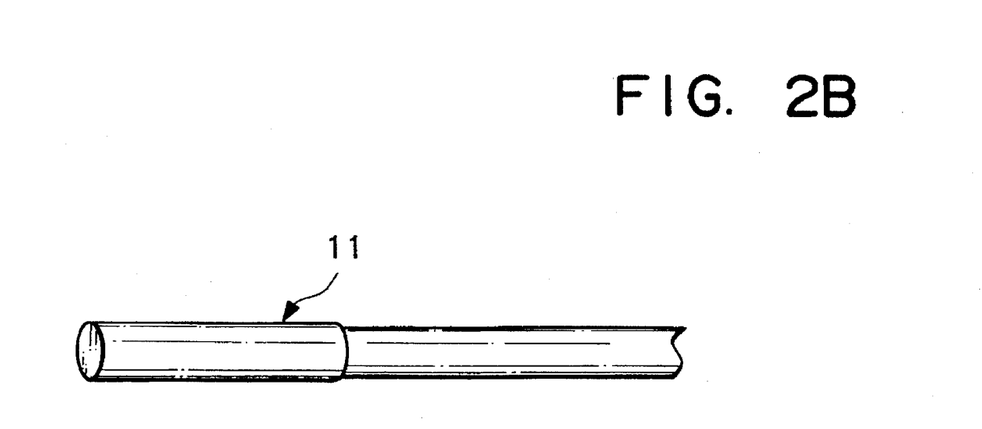

FIGS. 2A and 2B are views showing a catheter probe 11, in which FIG. 2A is a front view thereof and FIG. 2 is a perspective view showing the distal end portion of the catheter probe 11 of which diameter is about 1.5–2.5 mm. Referring to FIGS. 2A and 2B, reference numerals 201 and 202 denote optical fibers of which diameter is about 20–100 μm. One of the optical fibers serves as a radiation optical fiber, and the other optical fiber serves as a light incident optical fiber for receiving light reflected by blood, which light is included in all the radiated light components. The catheter probe 11 is inserted into, e.g., a pulmonary artery, to continuously measure the oxygen saturation.

Figure 3:
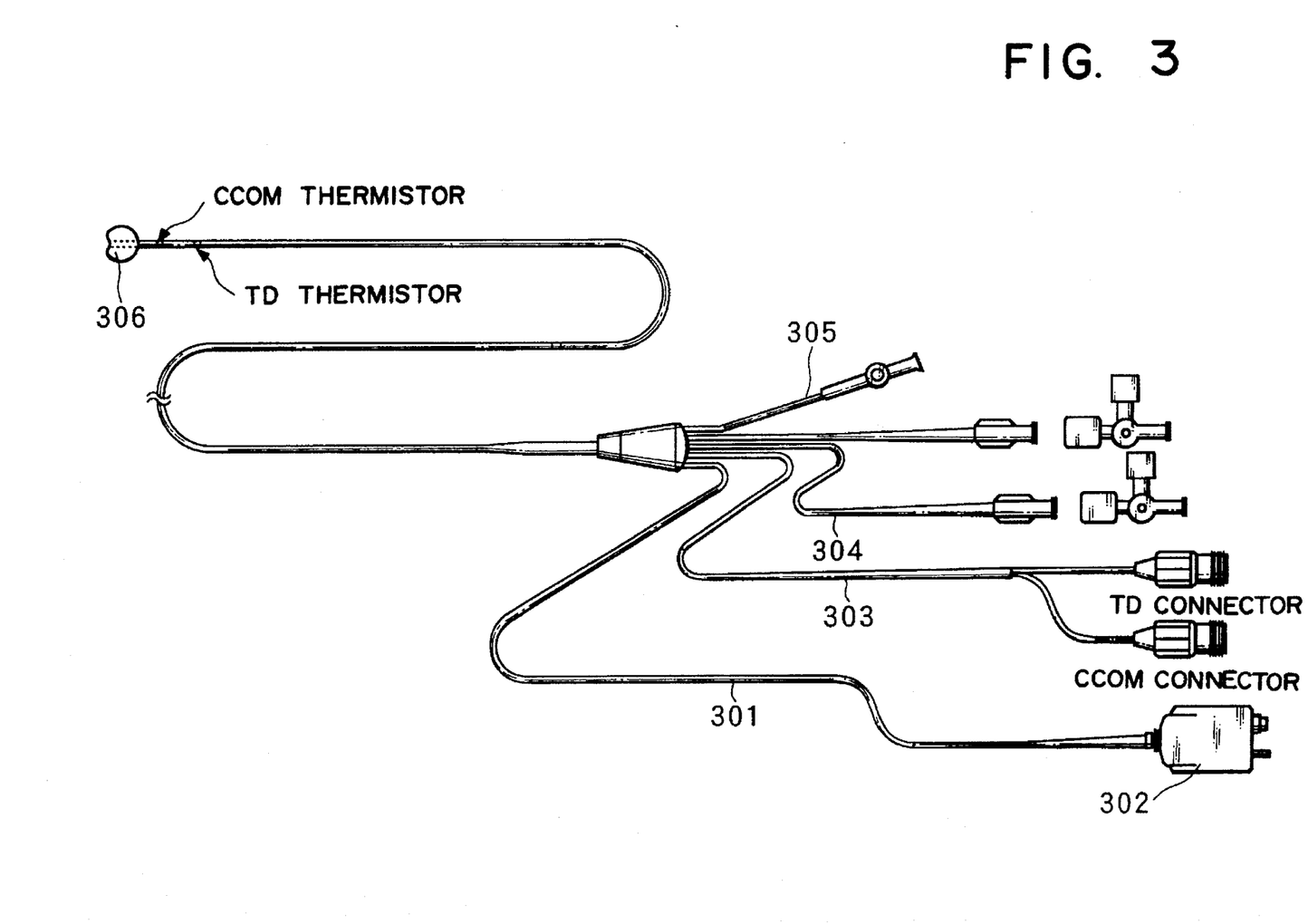
FIG. 3 is a view showing the outer appearance of the catheter probe connected to the oxygen saturation measuring apparatus of this embodiment.

FIG. 3 is a view showing the outer appearance of the catheter probe 11 used in this embodiment. Reference numeral 301 denotes an optical fiber; and 302, an optical connector plug connected to the oxygen saturation measuring apparatus in FIG. 1. Reference numeral 303 denotes an injection liquid line; 304, a line for measuring the pressure of the pulmonary artery; and 306, a balloon mounted at the distal end portion of the catheter. This balloon 306 is expanded by the pressure of air injected from a balloon expanding line 305 to define the distal end position of the catheter probe 11 in the blood vessel.

Description of Operation

In the apparatus of this embodiment, when the power switch is turned on, various initializing settings are performed. When the measurement preparation such as mounting of the catheter probe 11 is completed, the start switch of the operation unit 33 is turned on to start a measurement. Reflected light intensities of light components having the wavelengths of 600 nm (e.g., the frequency f1) and 805 nm (e.g., the frequency f2) are measured every 20 ms. The average value of several points is obtained to smooth the measurement values. Reflected light intensity signals normalized with the reference light intensities corresponding to the respective wavelengths, which are stored in the apparatus in advance, are obtained. These signals are defined as I1 and I2. The data of the signals I1 and I2 are stored in the measurement data area 35a in the RAM 35.

Measurement processing in the oxygen saturation measuring apparatus of this embodiment will be described with reference to the flow charts in FIGS. 4 and 5.

Figure 4:
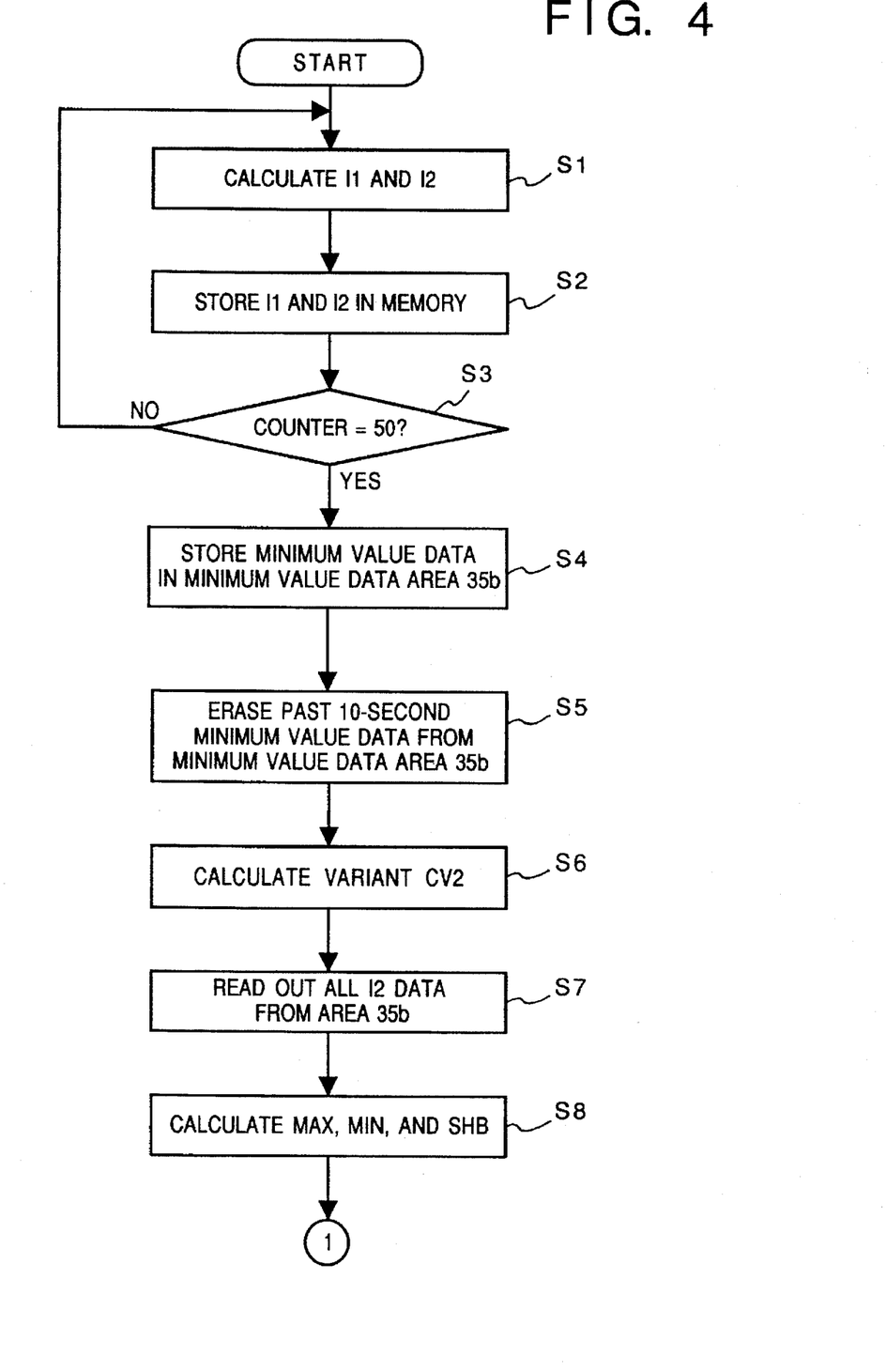
FIGS. 4 and 5 are flow charts showing measurement processing in an oxygen saturation measuring apparatus according to the first embodiment of the present invention.
Figure 5:
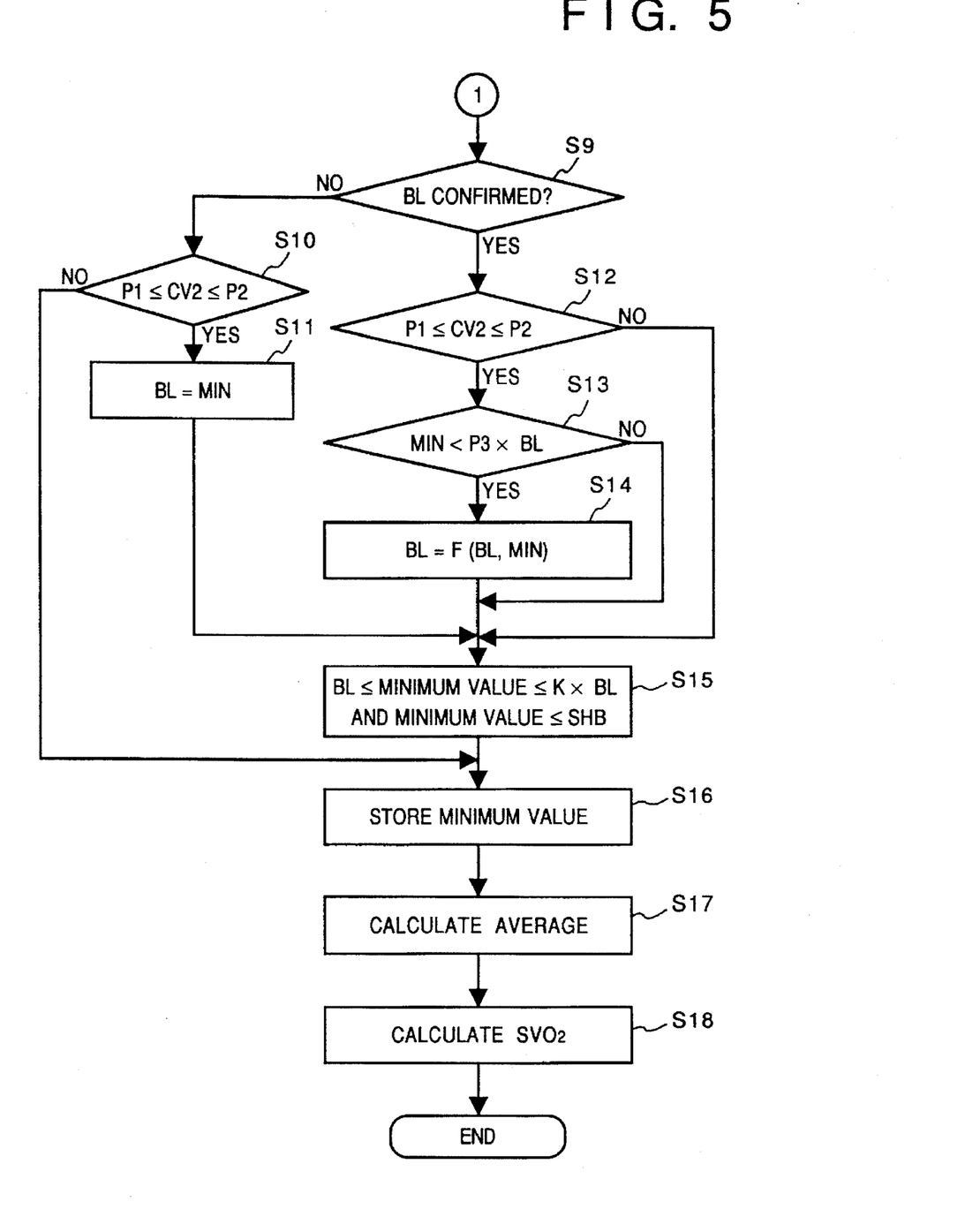

FIGS. 4 and 5 are the flow charts showing calculation processing in the oxygen saturation measuring apparatus of this embodiment. The control program for executing processing is stored in the ROM 34.

In step S1, the normalized reflected light intensity signals I1 and I2 are calculated. In step S2, the signals I1 and I2 are stored in the measurement data area 35a. These operations are repeated 50 times every 20 ms. When the number of measurement cycles is determined to be 50 in step S3, i.e., when a one-second measurement is completed, the flow advances to step S4.

The reflected light intensity signals measured by the catheter probe 11 periodically vary depending on blood flow pulsation and respiration. The variations depend not only the direct effect of the blood flow but also movement of the distal end portion of the catheter probe 11, which is caused by the blood flow and the respiration, resulting in reflection by the wall of the blood vessel. In many cases, the reflected light intensity increases due to the influence of the wall of the blood vessel. For this reason, only data representing the minimum values of the measured signals are used, the influences of the wall of the blood vessel can be reduced. In step S4, a minimum value is detected from 50 I2 data stored in the measurement data area 35a. A method of detecting this minimum value will be described below.

Of all the 50 (one second) data, every other data from the oldest one are used to obtain data change rates every 40 ms. If the signs of the data change rates exhibit a pattern of "−, −, +, +", the minimum value is confirmed to be present within this range. This can be explained using a symbol represented by an suffix $\underline{m}$, provided that the I2 data are numbered:

$$I2_{m-2} - I2_{m-4} < 0$$

$$I2_m - I2_{m-2} < 0$$

$$I2_{m+2} - I2_m > 0$$

$$I2_{m+4} - I2_{m+2} > 0$$

In this case, three points, i.e., $I2_{m-1}$, $I2_m$, and $I2_{m+1}$ are stored as minimum value data in the minimum value data area 35b in the RAM 35. Data of the corresponding reflected light intensity signal I1 are also stored in the same manner as described above. Note that a plurality of sign patterns each consisting of "−, −, +, +" may be detected in the 50 I2 data, or no pattern is detected therein.

In step S5, all the minimum value data stored 11 seconds ago are erased from the area 35b in the RAM 35. In this case, since minimum value detection is performed for each second, the data stored in the minimum value data area 35b are always the minimum value data for past 10 seconds from the current moment. In step S6, a parameter CV2 serving as an index representing the degree of variation in reflected light intensity in synchronism with the blood flow and respiration is calculated from the 50 I2 data stored in the measurement data area 35a. The calculated parameter CV2 is stored in the parameter area 35c in the RAM 35 for past 10 seconds from the current moment. A method of calculating the parameter CV2 will be described below.

First, variances $s^2$ of all the I2 data are obtained as follows:

$$I2(\text{MEANS}) = (1/50) \sum_{k=1}^{50} \cdot I2_k$$

$$\sigma^2 = (1/49) \cdot \sum_{k=1}^{50} (I2_k - I2(\text{MEANS}))^2$$

where I2 (MEANS) represents the average value of the 50 I2 data. The parameter CV2 calculated by the following equation is defined as a variation parameter. However, if such a parameter represents variations in data, another parameter defined by another equation representing a standard deviation or the like may be used:

$$CV2 = 100 \times (\sigma^2/I2 \,(\text{MEANS})^2)$$

In step S7, all the minimum value data of 10-second I2 data which are stored in the minimum value data area 35b are read out. In step S8, the parameters MAX, MIN, and SHB for determining the reference intensity BL (Base Level) in subsequent processing are calculated. The parameter MAX is a largest value of all the minimum value data of the I2 data which are stored in the minimum value data area 35b, and the parameter MIN is a smallest value thereof. The parameter SHB is a threshold value calculated using the parameters MAX and MIN as follows:

$$SHB = MIN + 0.66 \times (MAX - MIN)$$

Note that the constant of 0.66 is experimentally determined, but another constant may be used.

It is determined in step S9 whether the reference intensity BL is already determined. If NO in step S9, the flow advances to step S10 to determine whether all the past 10-second values of the variation parameter CV2 satisfy condition $P1 \leq CV2 \leq P2$. If YES in step S10, the flow advances to step S11 to determine the reference intensity BL as MIN. However, if NO in step S10, the flow advances to step S16. In this case, the constants P1 and P2 are threshold values for determining, on the basis of the values of the variation parameter CV2, a stable measurement state for minimizing the influence of light reflected by the wall of the blood vessel or the like. In this case, P1 is set to "0.09", and P2 is set to "3.0".

If it is determined in step S9 that the reference intensity BL is already determined, the flow advances to step S12 to determine whether all the past 10-second values of the variation parameter CV2 satisfy condition $P1 \leq CV2 \leq P2$. If YES in step S12, the flow advances to step S13; otherwise, the flow advances to step S15. In step S13, although the reflected light intensity is increased due to the influence of the wall of the blood vessel, the reference intensity BL is compared with MIN, assuming a state which cannot be determined by the variation parameter CV2, because the variation synchronized with the blood flow and respiration is relatively small. If MIN<P3×BL is satisfied, the flow advances to step S14 to update the reference intensity BL in accordance with the following equation. Otherwise, the flow advances to step S15. Note that the constant P3 is set to "1.8".

Reference Intensity BL=0.98×Reference Intensity BL+0.02×MIN

In this equation, the coefficients (0.98 and 0.02) are selected so that a new reference intensity BL relatively strongly depends on the previous non-updated reference intensity BL. However, other values can be selected.

In step S15, the total I2 minimum data stored in the minimum value data area 35b are further screened using the reference intensity BL and SHB which are determined as described above. It is determined whether all the minimum value data satisfy the condition of "BL≦Minimum Value≦K×BL," in order to extract the Minimum Value data in a predetermined range. Minimum value data satisfying this condition are left, and minimum value data which do not satisfy the condition are discarded. It is then determined whether the remaining minimum value data satisfy condition (Minimum Value)≦SHB. Minimum value data satisfying this condition are left, and other data are discarded. In this case, the constant K is set to "1.8".

The flow advances to step S16 to store reflected light intensity data I1 together with the I2 minimum value data selected in step S15. The flow advances to step S17 to obtain an average value M1 (average value of the I1 minimum value data) and an average value M2 (average value of the I2 minimum value data) The M1 and M2 are substantially the moving averages of the minimum value data in a predetermined time period. In step S18, the value of the oxygen saturation ($SVO_2$) is calculated in accordance with the following equation:

$$SVO_2 = \sum_{n=0}^{3} a_n \times (M2/M1)^n$$

where $a_n$ is an experimentally determined constant.

$a_0 = 141.2$
$a_1 = -23.10$
$a_2 = -51.38$
$a_3 = 14.72$

According to this embodiment, a signal which is less influenced by reflection from a blood vessel or the like is discriminated using the minimum value data of the reflected light intensity signals I1 and I2, the parameters MIN, MAX, and SHB obtained from the variation parameter CV2 and the minimum value data, and the reference intensity BL obtained using these parameters. The oxygen saturation ($SVO_2$) is calculated to accurately measure the $SVO_2$.

As has been described above, according to this embodiment, the influences of light reflected by the wall of the blood vessel except for the blood can be eliminated, and the oxygen saturation of the blood can be precisely measured.

Figure 6:
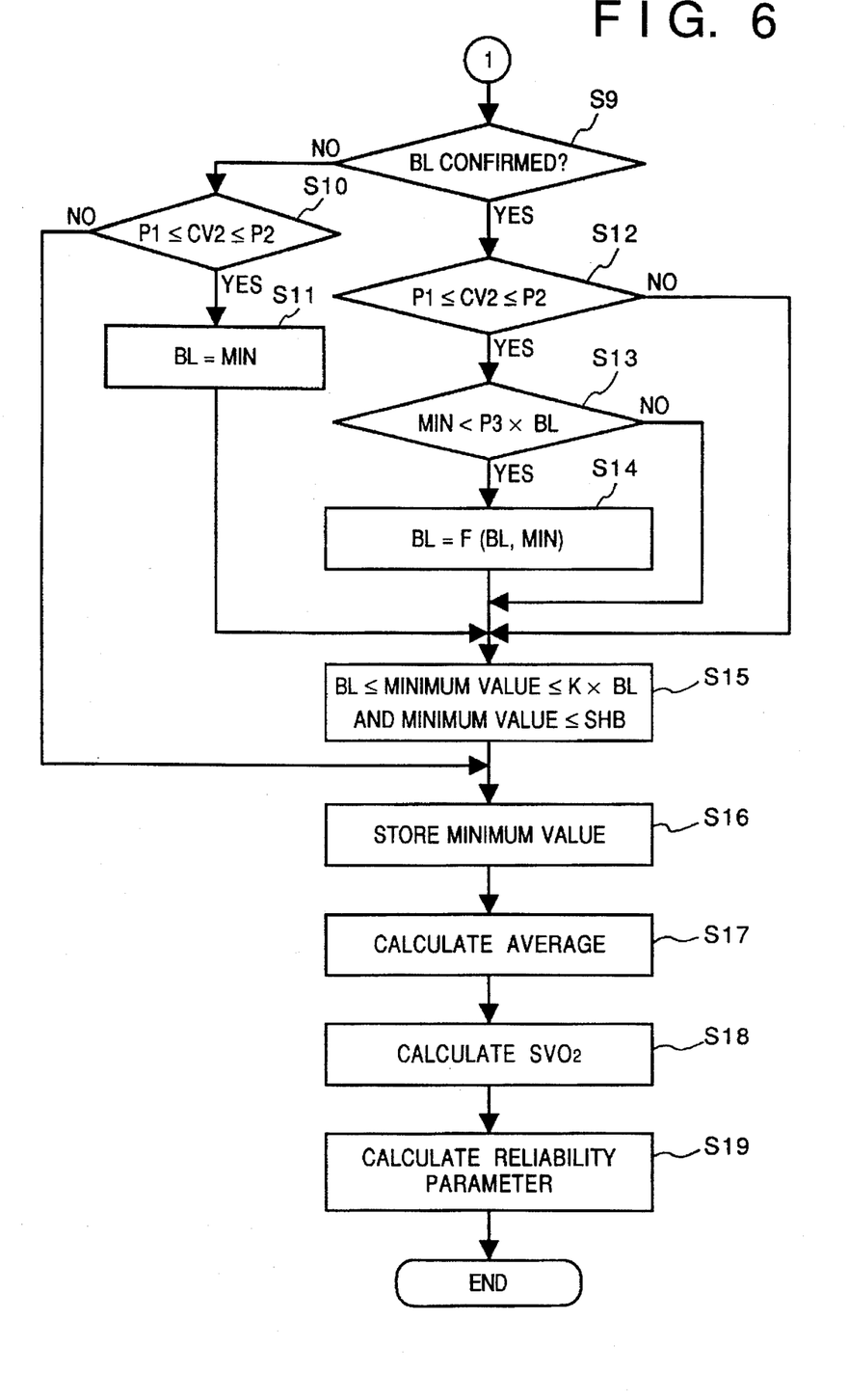
FIG. 6 is a flow chart showing measurement processing in an oxygen saturation measuring apparatus according to the second embodiment of the present invention.

FIG. 6 is a flow chart showing measurement processing of an oxygen saturation according to the second embodiment of the present invention. Steps S1 to S8 are the same as those in the first embodiment, and a detailed description and drawing thereof will be omitted. Steps S9 to S18 in FIG. 6 are the same as those in FIG. 5, and a detailed description thereof will be omitted. The characteristic feature of the second embodiment lies in that a parameter (to be referred to as a reliability parameter SRP hereinafter) representing the degree of reliability of the calculated oxygen saturation is calculated using a parameter MIN, a reference intensity BL, and a parameter CV2, all of which are calculated in the previous steps.

A practical method of calculating the reliability parameter SRP will be described below.

Figure 7:
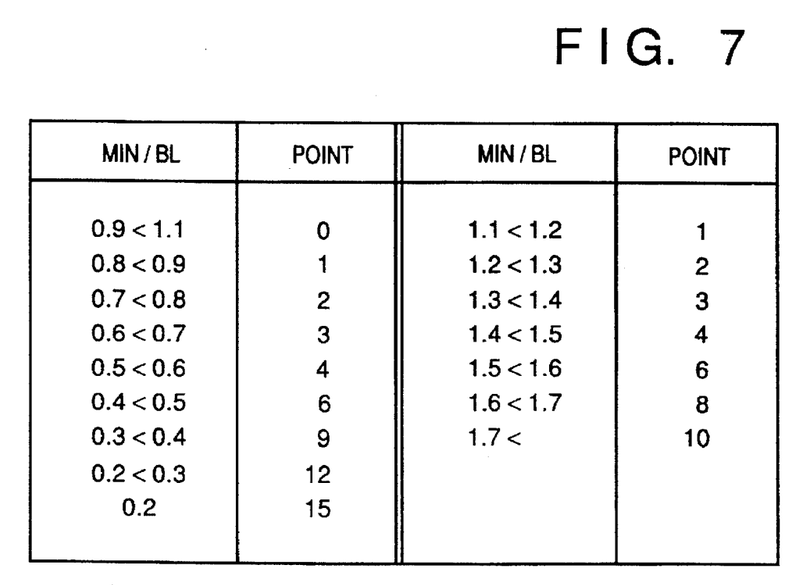
FIG. 7 is a table showing the settings of points corresponding to a ratio of a parameter MIN to a reference intensity BL.

As shown in FIG. 7, values of the ratio of the parameter MIN to the reference intensity BL are divided into several ranges. These ranges are caused to correspond to predetermined numerical values (to be referred to as points hereinafter). These points are stored as a table in a ROM 34. A point stored in the ROM 34 is selected in accordance with a calculated ratio (MIN/BL).

The ratio (MIN/BL) may serve as an index for monitoring that the distal end of a catheter is constrained to disable continuous detection of reflected light signals from blood due to various causes except for periodical variations (e.g., variations synchronized with a blood flow and respiration) of the reflected light intensity, or for monitoring influences caused by disconnection and kinking (bending) of an optical fiber in the catheter.

Figure 8:
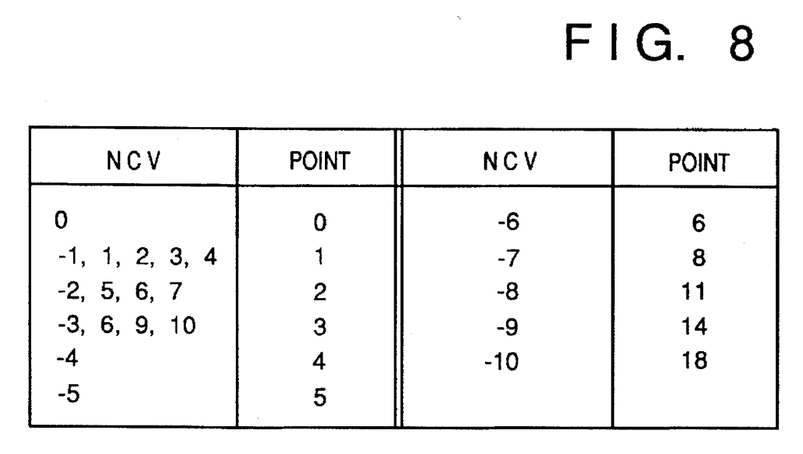
FIG. 8 is a table showing the correspondence between a parameter NCV and points.

The following classification is performed for variant parameter CV2 of each block. If classification values are defined as −1, 0, and +1, a total value of values corresponding to the past 10-second values of the variant parameter CV2 is defined as a parameter NCV:

if CV2<0.06, then −1
if 0.06≦CV2≦3.00, then 0
if 3.00<CV2, then +1

As shown in FIG. 8, points corresponding to the respective NCV values are predetermined in the same manner as described above. A table which stores these data is stored in the ROM 34, and a point corresponding to each calculated parameter NCV value can be obtained.

In this case, the parameter NCV is regarded as a parameter for monitoring periodic variations of the reflected light intensity.

Figure 9:
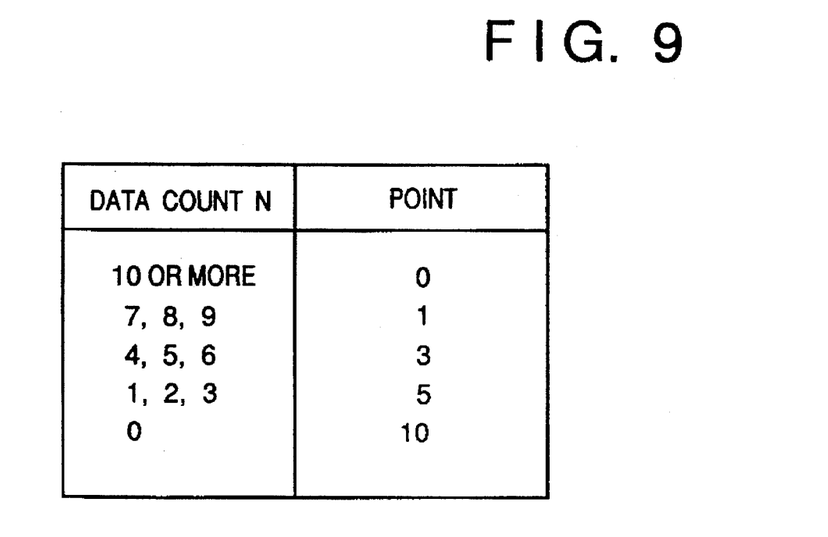
FIG. 9 is a table showing the correspondence between a minimum value data count N and points.

A correspondence between the minimum value data count N, i.e., data count N used in calculating the oxygen saturation, selected in step S15, and the points is also set. A point corresponding to the calculated data count N can be obtained with reference to the table. In this case, the data count N is regarded as an index for monitoring the S/N ratio of the oxygen saturation to be calculated.

Figure 10:
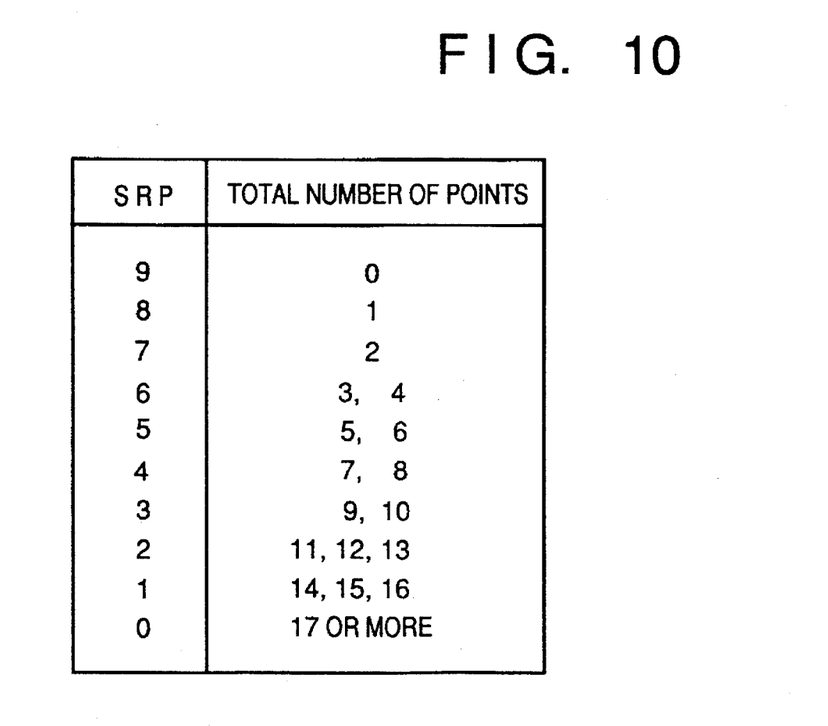
FIG. 10 is a table showing the correspondence between a reliability parameter and total points.

The reliability parameter SRP can be represented by a total value of the above points, as shown in FIG. 10.

A larger value indicates a higher degree of reliability. The reliability parameter SRP is calculated as a total number of points corresponding to the three parameters MIN/BL, NCV, and N. The above processing is plausible when the meanings of these three parameters are considered.

The reliability parameter calculated as described above may be displayed in, e.g., a numerical value or level together with the measurement value to the operator or observer at the monitor, or may be informed by any other means such as a volume level, a scale, or a change in time interval of intermittent sounds, output from a speaker 40. The degree of reliability of the measurement value can be grasped, and erroneous decision and treatment based on the measurement value can be prevented.

According to this embodiment, a signal which is less influenced by reflection from a blood vessel or the like is discriminated using the minimum value data of the reflected light intensity signals I1 and I2, the parameters MIN, MAX, and SHB obtained from the variation parameter CV2 and the minimum value data, and the reference intensity BL obtained using these parameters. A more accurate oxygen saturation ($SVO_2$) is calculated to accurately measure the $SVO_2$.

As still another embodiment, the above processing may also be applied to a blood flow measuring apparatus or the like which uses a velocity sensor incorporated in, e.g., a cardiac catheter. As in the measurement of the oxygen saturation, when the velocity sensor is brought into contact with the wall of a blood vessel, a measurement error apparently occurs. The present invention can be used as a reliability monitor for the velocity sensor. For example, in a velocity sensor described in Japanese Patent Laid-Open No. 3-221815, a change in heat radiation depending on the velocity of a self-heated thermistor is measured as a change in temperature. When the velocity sensor is brought into contact with the wall of the blood vessel, heat dissipation is avoided to cause an error due to an increase in temperature. The thermistor used as the velocity sensor is of an NTC type which has a resistance value reduced with an increase in temperature. The temperature is measured as the resistance of the thermistor, and the error occurs in a direction to reduce the resistance value. Therefore, the maximum value of the resistance of the thermistor is detected, a reference intensity signal is determined from the maximum value, and the same processing as in the above embodiments is performed, thereby calculating a parameter representing the degree of reliability of the measurement value.

As can be apparent from the above description, the present invention is also applicable as an apparatus for monitoring the degree of reliability of a measurement value using a sensor (e.g., a pressure or temperature sensor) whose precision of the measurement value is degraded when the sensor is brought into contact with or comes close to the wall or the blood vessel of the like.

As has been described above, according to the embodiments of the present invention, since the degree of influences of light reflected by the wall of the blood vessel except for the blood can be evaluated, and the degree of reliability of the measurement value can be informed together with the measurement result to the operator, the reliability of the measurement value can be improved, and erroneous decision and treatment can be prevented.

Other many widely different embodiments of the present invention can be made without departing from the spirit and scope thereof, it is to be understood that the invention is not limited to the specific embodiments thereof except as defined in the appended claims.

What is claimed is:

1. A measuring apparatus comprising:

radiating means for radiating light having first and second wavelengths different from each other in blood;

detecting means for detecting reflected light intensities from the blood upon radiation of the light having the first and second wavelengths;

minimum value detecting means for detecting a minimum value of the reflected light intensity of one of the light having the first and second wavelengths detected by said detecting means within a predetermined period of time; and calculating means for calculating an oxygen saturation on the basis of the minimum value detected by said minimum value detecting means and a minimum value of the reflected light intensity of the other light corresponding to the minimum value detected by said minimum value detecting means.

2. An apparatus according to claim 1, wherein said radiating means radiates the light in the blood from a distal end of a catheter through an optical fiber.

3. An apparatus according to claim 2, wherein said detecting means guides the light incident on the distal end of said catheter to a photosensor through an optical fiber.

4. An apparatus according to claim 1, wherein said minimum value detecting means sequentially calculates differences between reflected light intensities of two points adjacent on a time axis within the predetermined period of time to express calculated differences as signs, and defines, as the minimum value, a central one of five points having a pattern of "−, −, +, +" of the reflected light intensities.

5. An apparatus according to claim 1, wherein said calculating means comprises:

parameter calculating means for calculating a parameter representing a variation of the reflected light intensities which corresponds to one of the light components having the first and second wavelengths within a first predetermined period of time;

means for obtaining a smallest value of the minimum values calculated by said minimum value detecting means within a second predetermined period of time; and reference value calculating means for calculating a reference value from the parameter and the smallest value, wherein the oxygen saturation is obtained on the basis of the minimum values which are within a predetermined range from the reference value.

6. An apparatus according to claim 5, wherein the reference value is determined on the basis of the smallest value and changed in accordance with a current reference value and the smallest value when the parameter is within the second predetermined period of time.

7. An apparatus according to claim 5, wherein said calculating means calculates the oxygen saturation as follows:

$$SvO2 = \sum_{n=0}^{3} a_n \times (M2/M1)^n$$

for
$a_0=141.2$
$a_1=-23.10$
$a_2=-51.38$
$a_3=14.72$ where M2 is an average value of the minimum values which are within a predetermined range from the reference value, and M1 is an average value of the reflected light intensity of the light of another wavelength.

8. A measuring apparatus comprising:

detecting means for detecting a signal intensity from a probe inserted into a blood vessel;

extremum detecting means for calculating a minimum value and/or a maximum value of the signal intensity detected by said detecting means within a first predetermined time period;

measuring means for calculating a measurement value on the basis of the minimum value and/or the maximum value;

calculating means for calculating a smallest value of the minimum values and/or a largest value of the maximum values in a second predetermined time period;

reference intensity signal determining means for determining a reference intensity signal on the basis of the smallest value and/or the largest value; and parameter calculating means for calculating a parameter for evaluating a degree of reliability of the measurement value measured by said measuring means, on the basis of the smallest value and/or the largest value, and the reference intensity signal.

9. An apparatus according to claim 8, wherein the signal intensity detected by said detecting means is an intensity of light reflected by the blood upon radiation of light into the blood by radiating means.

10. An apparatus according to claim 8, wherein said extremum detecting means sequentially calculates differences between reflected light intensities of two points adjacent on a time axis within a third predetermined period of time to express calculated differences as signs, and defines, as the minimum value, a central one of five points having a pattern of "−, −, +, +" of the reflected light intensities.

11. An apparatus according to claim 8, wherein the measurement value calculated by said measuring means is one of the oxygen saturation in the blood, a blood flow rate, and a measurement value obtained by measuring living body information on the basis of a signal from a sensor located near a blood-side end of an optical fiber.

12. An apparatus according to claim 8, further comprising alarming means for alarming the degree of reliability of a measurement value based on the parameter calculated by said parameter calculating means.

13. A measuring apparatus comprising:

detecting means for detecting a signal intensity from a probe inserted into a blood vessel;

extremum detecting means for calculating a minimum value and/or a maximum value of the signal intensity detected by said detecting means within a first predetermined period of time;

calculating means for calculating a smallest value of the maximum value and/or largest values of the maximum values in a second predetermined period of time;

variation parameter calculating means for calculating a changing parameter representing a degree of change of the reflected light intensity in the second predetermined period of time;

reference intensity signal determining means for determining a reference intensity signal on the basis of the smallest value and/or the largest value and the variation parameter; and parameter calculating means for calculating a parameter for evaluating a degree of reliability of a measurement value, on the basis of the smallest value and/or the largest value, and the changing parameter and the reference intensity signal.

14. An apparatus according to claim 13, wherein said variation parameter calculating means defines a standard deviation, a variation coefficient, or a function thereof as the variation parameter.

15. An apparatus according to claim 14, wherein said reference signal calculating means updates the reference value to a new reference value in accordance with a predetermined function when the variation parameter falls within a predetermined range, and does not update the reference value when the variation parameter falls outside the predetermined range.

16. An apparatus according to claim 13, wherein the measurement value calculated by said measuring means is one of the oxygen saturation in the blood, a blood flow rate, and a measurement value obtained by measuring living body information on the basis of a signal from a sensor located near a blood-side end of an optical fiber.

17. A measuring apparatus comprising:

an optical fiber for transmitting light into a blood vessel;

radiating means, connected to said optical fiber, for radiating the light into blood;

reflected light intensity detecting means, connected to said optical fiber, for detecting a reflected light intensity from the blood;

minimum value detecting means for detecting a minimum value of the reflected light intensity detected by said reflected light intensity detecting means in a first predetermined period of time;

smallest value calculating means for calculating a smallest value (MIN) of the minimum values within a second predetermined period of time longer than the first predetermined period of time;

variation parameter calculating means for calculating a variation parameter (CV2) representing a degree of variation of the reflected light intensity within the first predetermined period of time;

parameter calculating means for combining the smallest value (MIN) and the variation parameter (CV2), and a reference intensity signal (BL) determined by the smallest value and the variation parameter, and calculating a plurality of parameters for evaluating a degree of reliability of a separately calculated measurement value; and evaluating means for calculating one parameter for evaluating the degree of reliability of the measurement value from a sum total (SRP) of the plurality of parameters.

* * * * *

UNITED STATES PATENT AND TRADEMARK OFFICE
CERTIFICATE OF CORRECTION

PATENT NO. : 5,647,359
DATED : July 15, 1997
INVENTOR(S) : Hiromasa KOHNO et al

It is certified that error appears in the above-identified patent and that said Letters Patent is hereby corrected as shown below:

Title page, item [57], line 4, delete "Bight" and insert -- Light --.

Signed and Sealed this

Seventeenth Day of February, 1998

Attest:

BRUCE LEHMAN

*Attesting Officer*  *Commissioner of Patents and Trademarks*